United States Patent
Kanzaki et al.

(10) Patent No.: US 8,279,432 B2
(45) Date of Patent: Oct. 2, 2012

(54) PARTICLE INSPECTION AND REMOVAL APPARATUS AND PARTICLE INSPECTION AND REMOVAL PROGRAM

(75) Inventors: Toyoki Kanzaki, Kyoto (JP); Kunio Ohtsuki, Kyoto (JP)

(73) Assignee: Horiba, Ltd. (JP)

( * ) Notice: Subject to any disclaimer, the term of this patent is extended or adjusted under 35 U.S.C. 154(b) by 384 days.

(21) Appl. No.: 12/721,865

(22) Filed: Mar. 11, 2010

(65) Prior Publication Data
US 2010/0229902 A1   Sep. 16, 2010

(30) Foreign Application Priority Data
Mar. 11, 2009   (JP) .................. 2009-058765

(51) Int. Cl.
*G01N 21/00*   (2006.01)
(52) U.S. Cl. ............... 356/237.3; 356/237.4; 356/237.5
(58) Field of Classification Search .... 356/237.1–241.6, 356/242.1–243.8, 426–431, 600–640
See application file for complete search history.

(56) References Cited

U.S. PATENT DOCUMENTS

| | | | | |
|---|---|---|---|---|
| 4,468,120 A | * | 8/1984 | Tanimoto et al. | 356/239.8 |
| 5,399,867 A | * | 3/1995 | Kohno | 250/461.1 |
| 5,634,230 A | * | 6/1997 | Maurer | 15/1.51 |
| 7,135,344 B2 | * | 11/2006 | Nehmadi et al. | 438/14 |

FOREIGN PATENT DOCUMENTS

| | | |
|---|---|---|
| JP | 2006-10544 A | 1/2006 |
| JP | 2006-300705 A | 11/2006 |

* cited by examiner

*Primary Examiner* — Gregory J Toatley
*Assistant Examiner* — Jarreas C Underwood
(74) *Attorney, Agent, or Firm* — Cantor Colburn LLP

(57) ABSTRACT

The present invention is to lessen work burden on a user, to eliminate determination error, to prevent a substrate from being damaged, and to prevent prolonged working time by automatically determining whether or not a particle to be removed is present. A particle inspection and removal apparatus of the present invention includes a particle information acquisition section acquiring particle information on a particle adhering onto a substrate surface, a particle removal section removing the particle adhering onto the substrate surface, a comparison section comparing a threshold set for each of regions of the substrate surface with the particle information on each of the region obtained by the particle information acquisition section, and a particle removal control section controlling the particle removal section to remove the particle on the substrate surface based on a comparison result of the comparison section.

2 Claims, 5 Drawing Sheets

PARTICLE INSPECTION AND REMOVAL APPARATUS AND PARTICLE INSPECTION AND REMOVAL PROGRAM

BACKGROUND OF THE INVENTION

1. Field of the Invention

The present invention relates to a particle inspection and removal apparatus and a particle inspection and removal program for inspecting a particle adhering onto a surface of a substrate such as a reticle for transferring a circuit pattern onto a semiconductor wafer and removing the particle.

2. Description of the Background Art

As a particle inspection apparatus inspecting a particle on a surface of a substrate, there is known the following particle inspection apparatus as disclosed in Patent document 1. The particle inspection apparatus includes an irradiation optical system irradiating inspection light onto the surface of the substrate, a detection optical system detecting reflected and scattered light by the surface of the substrate, and an information processing device determining whether or not a particle is present on the surface of the substrate based on a light intensity signal obtained by the detection optical system.

Conventionally, if an inspection result of this particle inspection apparatus indicates that a particle is present on the surface of the substrate, the particle is temporarily taken out from within the particle inspection apparatus and removed by user's manual operation using an air gun.

However, when the particle adhering onto the surface of the substrate is removed by user's manual operation, the substrate is possibly damaged. Due to this, it is necessary for an experienced and skilled operator to remove the particle. If the substrate is a reticle with a pellicle, extreme caution is required to remove the particle by manual operation because a pellicle tends to be damaged. Furthermore, since a user determines whether to remove the particle, to confirm whether or not it is necessary to perform a particle removal operation is disadvantageously complicated. Besides, there is a possible determination error depending on the user, and some user possibly overlooks the particle to be removed.

In some cases, not the user but the particle inspection apparatus determines whether or not a particle is present and removes the particle. In this case, the particle inspection apparatus often makes a uniform determination irrespective of types of regions on the substrate.

In a region where a fine circuit pattern is formed, it is necessary to remove even a small particle. In a region where a coarse circuit pattern is formed or where no circuit pattern is formed, it is not always necessary to remove a small particle. In this way, whether to remove a particle or not depends on the region of the surface of the substrate. If the uniform determination is made to detect a particle of a predetermined size uniformly, a removal operation for removing a particle that is not always necessary to remove is performed, disadvantageously resulting in an increase in working time.

Patent document 1: Japanese Unexamined Patent Publication No. 2006-10544

Patent document 2: Japanese Unexamined Patent Publication No. 2006-300705

SUMMARY OF THE INVENTION

The present invention has been made to solve all the conventional problems. It is a main object of the present invention to lessen work burden on a user, to eliminate determination error, and to prevent prolonged working time by automatically determining whether or not a particle to be removed is present.

Namely, a particle inspection and removal apparatus according to one aspect of the present invention includes:

(1) a particle information acquisition section acquiring particle information on a particle adhering onto a substrate surface.

(2) a particle removal section removing the particle adhering onto the substrate surface.

(3) a comparison section comparing a condition for particle removal set for each of a plurality of regions on the substrate surface with the particle information on each of the regions obtained by the particle information acquisition section.

(4) a particle removal control section controlling the particle removal section to remove the particle on the substrate surface if a comparison result of the comparison section indicates that the particle information satisfies the condition.

The particle inspection and removal apparatus configured as stated above determines whether to remove a particle for every region of the substrate surface by setting the condition for each region of the substrate surface and removing the particle only if the magnitude of the particle exceeds the condition. It is possible to dispense with unnecessary particle removal operation. Therefore, the number of times of cleaning of the substrate including the particle removal operation can be reduced, working time can be prevented from being prolonged, and running cost can be reduced. In addition, the particle inspection and removal apparatus automatically determines such particle information as the magnitude of the particle or the number of particles without causing a user to make such a determination. Therefore, it is possible to eliminate determination error of each user. Besides, not the user but the particle inspection and removal apparatus performs the removal operation mechanically. This can lessen burden on the user, reduce risk of damage of the substrate W, and dispense with removal skill.

It is preferable that the substrate is a reticle for transferring a circuit pattern onto a semiconductor wafer or a reticle with a pellicle, and that the regions are set for different circuit patterns formed on the reticle. If the substrate is a reticle for transferring a circuit pattern onto a semiconductor wafer or a reticle with a pellicle, and the regions are set for different circuit patterns formed on the reticle, advantages of the present invention can be exhibited more conspicuously even if the allowed magnitude of the adhering particle differs depending on a size of a circuit pattern formed on the reticle. In addition, the pellicle-attached reticle has the problem that the pellicle is easily damaged particularly if the user cleans the pellicle. In contrast, by causing the particle inspection and removal apparatus to perform particle removal operation, it is possible to prevent the pellicle from being damaged, to reduce the number of times of pellicle replacement, and to greatly reduce running cost. Besides, by determining whether or not to allow an adhering particle for every circuit pattern, it is possible to reduce the number of times of cleaning, to prolong a service life of the circuit pattern itself formed on the reticle, and to thereby reduce cost required for the reticle.

A program according to another aspect of the present invention is a particle inspection and removal program for inspecting and removing a particle adhering onto a substrate surface using a particle information acquisition section acquiring particle information on a particle adhering onto a substrate surface and a particle removal section removing the particle adhering onto the substrate surface, the particle inspection and removal program causing a computer to function as: a comparison section comparing a condition for particle removal set for each of a plurality of regions on the substrate surface with the particle information on each of the regions obtained by the particle information acquisition section; and a particle removal control section controlling the particle removal section to remove the particle on the substrate surface if a comparison result of the comparison section indicates that the particle information satisfies the condition.

According to the present invention constituted as stated above, it is possible to lessen work burden on a user, to eliminate determination error, to prevent a substrate from being damaged, and to prevent prolonged working time by automatically determining whether or not a particle to be removed is present.

DESCRIPTION OF THE PREFERRED EMBODIMENTS

A particle inspection and removal apparatus according to an embodiment of the present invention will be described hereinafter.

<Apparatus Configuration>

Figure 1:
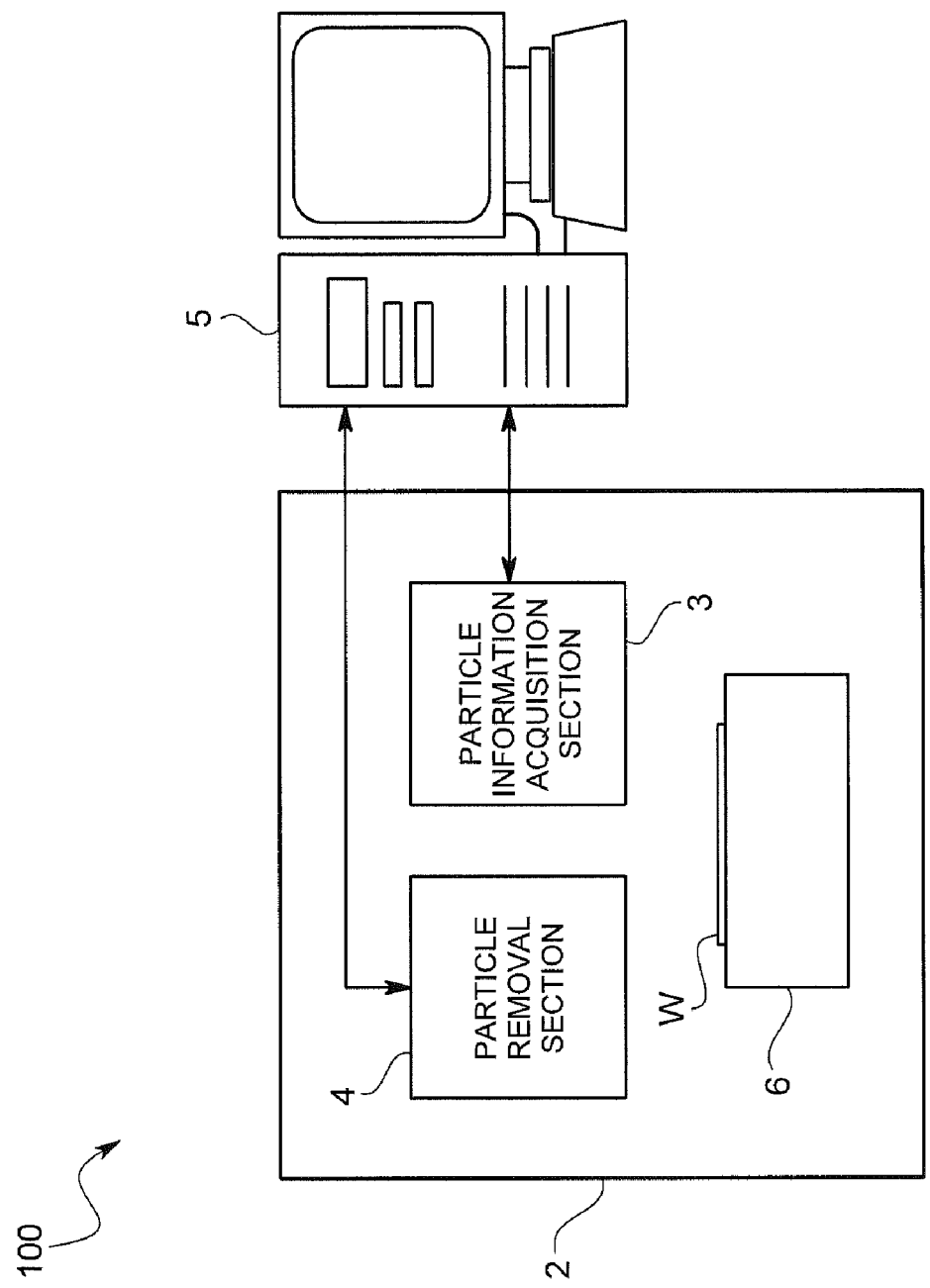
FIG. 1 is an overall configuration diagram according to an embodiment of the present invention.

A particle inspection and removal apparatus 100 according to the embodiment of the present invention inspects and removes a particle that adheres onto a surface W1 (also referred to as "substrate surface W1", hereinafter) of a substrate W that is a reticle for transferring a circuit pattern onto, for example, a semiconductor wafer, onto which reticle a pellicle serving as a protection film is attached and that is observed in the pellicle. As shown in FIG. 1, the particle inspection and removal apparatus 100 includes a mount 2, a particle information acquisition section 3 acquiring particle information on the substrate surface W1, a particle removal section 4 removing a particle adhering onto the substrate surface W1, and an information processing device 5 acquiring an output signal from the particle information acquisition section 3, calculates the particle information on the substrate surface W1, and controlling the particle removal section 4 based on the particle information. This particle inspection and removal apparatus 100 is configured to have a mini-environment structure having the particle information acquisition section 3 and the particle removal section 4 accommodated in one mount 2.

Figure 2:
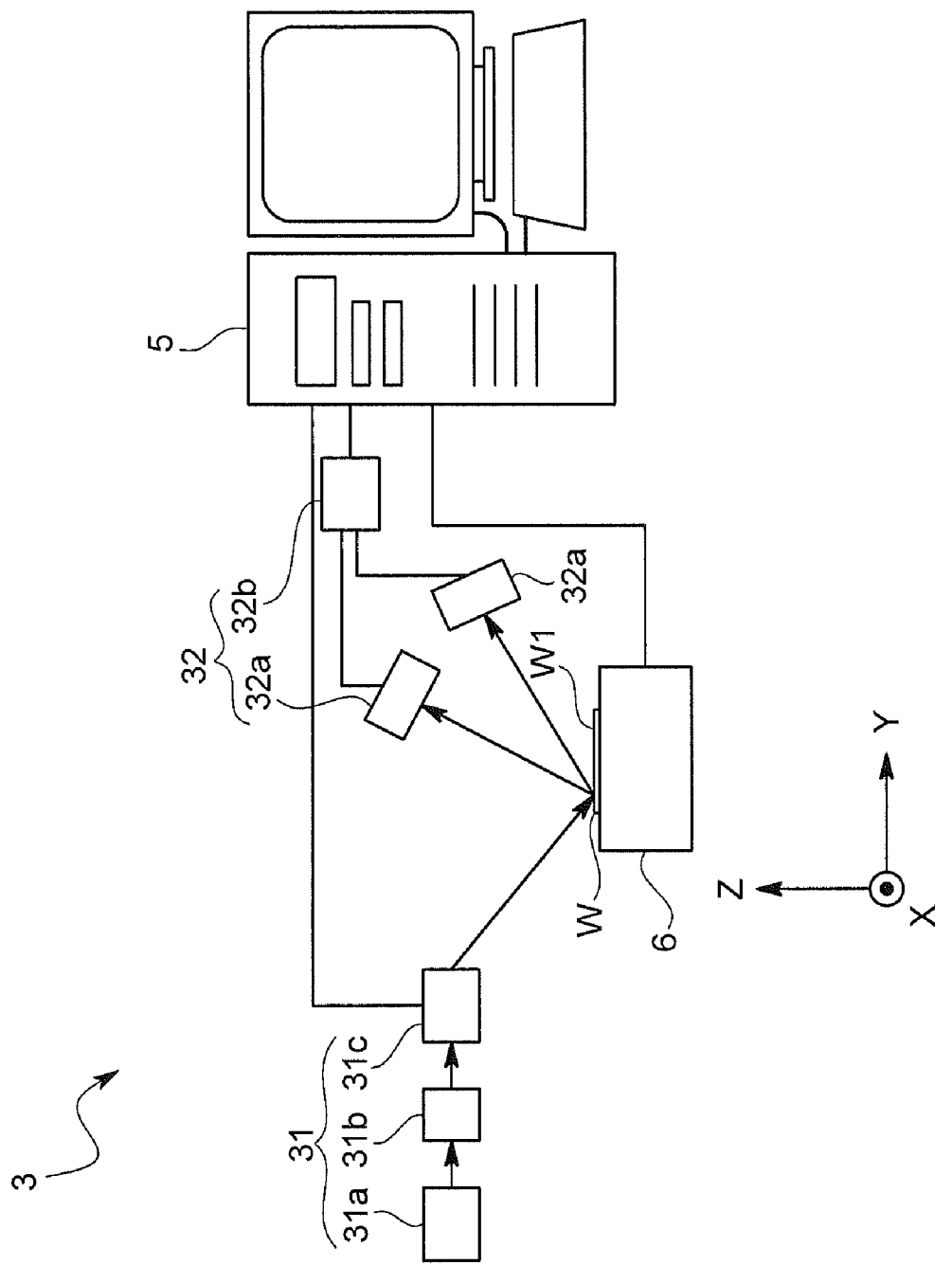
FIG. 2 is a pattern diagram showing a configuration of a particle information acquisition section according to the embodiment.

The particle information acquisition section 3 is a light scattering acquisition section for acquiring particle information including presence or absence of a particle adhering onto the substrate surface 1, a magnitude, a position and the like of the particle. As shown in FIG. 2, the particle information acquisition section 3 includes a light irradiation section 31 irradiating inspection light onto the surface W1 of the substrate W mounted on a movable stage 6 while scanning the inspection light, and a light detection section 32 detecting a reflected and scattered light by the substrate surface irradiated with the inspection light.

The movable stage 6 is movable in X, Y, and Z directions, and controlled to move in the Y direction at constant velocity during an inspection by a particle inspection control section 51 of the information processing device 5 to be described later. A reticle with a pellicle W or the like serving as the substrate is mounted on an upper surface of the movable stage 6 horizontally. The movable stage 6 is controlled to move at constant velocity in the X and Y directions during particle removal by a particle removal control section 55 of the information processing device 5 to be described later.

The light irradiation section 31 irradiates the inspection light onto the reticle W mounted on the movable stage 6 while scanning the inspection light. The light irradiation section 31 includes a light source 31a that emits laser light, a scanning mirror 31b scanning the laser beam in the X direction, and a light focusing optical system 31c. The light irradiation section 31 is configured to irradiate the laser light from the light source 31a onto the inspection target, that is, surface W1 of the reticle W from obliquely upward of a predetermined angle with respect to the inspection target while linearly scanning the laser light in the X direction (direction perpendicular to a sheet of FIG. 2) in a reciprocating fashion. In the present embodiment, a laser tube such as an HeNe laser tube is used as the light source 31a. The scanning mirror 31b is controlled by the particle inspection control section 51 of the information processing device 5 to be described later.

The light detection section 32 detects the reflected and scattered light by the substrate surface W1. In the present embodiment, two light detection sections 32 are arranged obliquely upward of the inspection target W by a holding member (not shown). Each light detection section 32 is configured to include a focusing lens (not shown), a fixed slit plate (not shown) including an incident light limiting slit for the reflected and scattered light, and a light detector 32a (such as a photomultiplier). Each light detection section 32 also includes a signal processor 32b.

Figure 3:
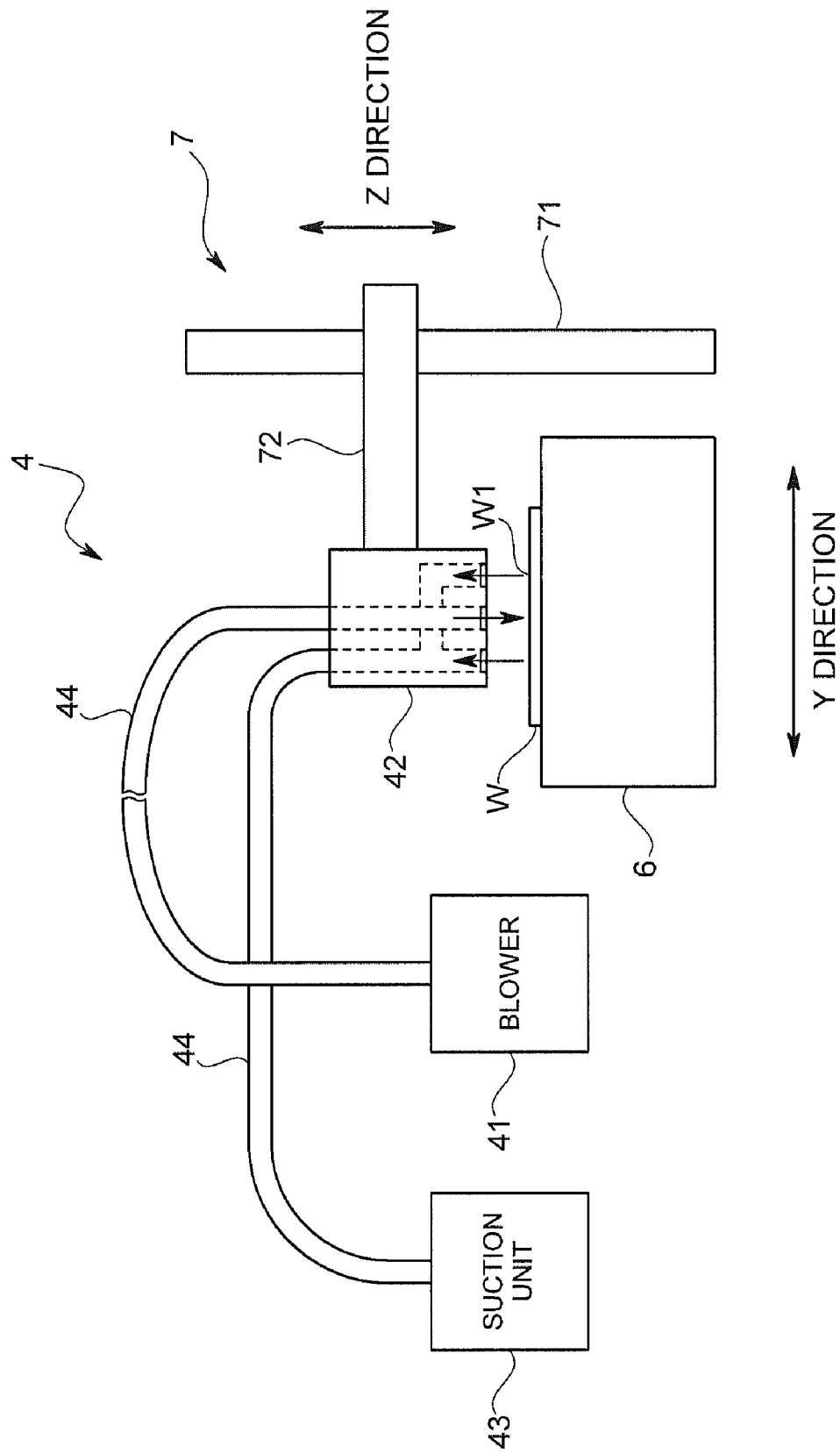
FIG. 3 is a pattern diagram showing a configuration of a particle removal section according to the embodiment.
Figure 4:
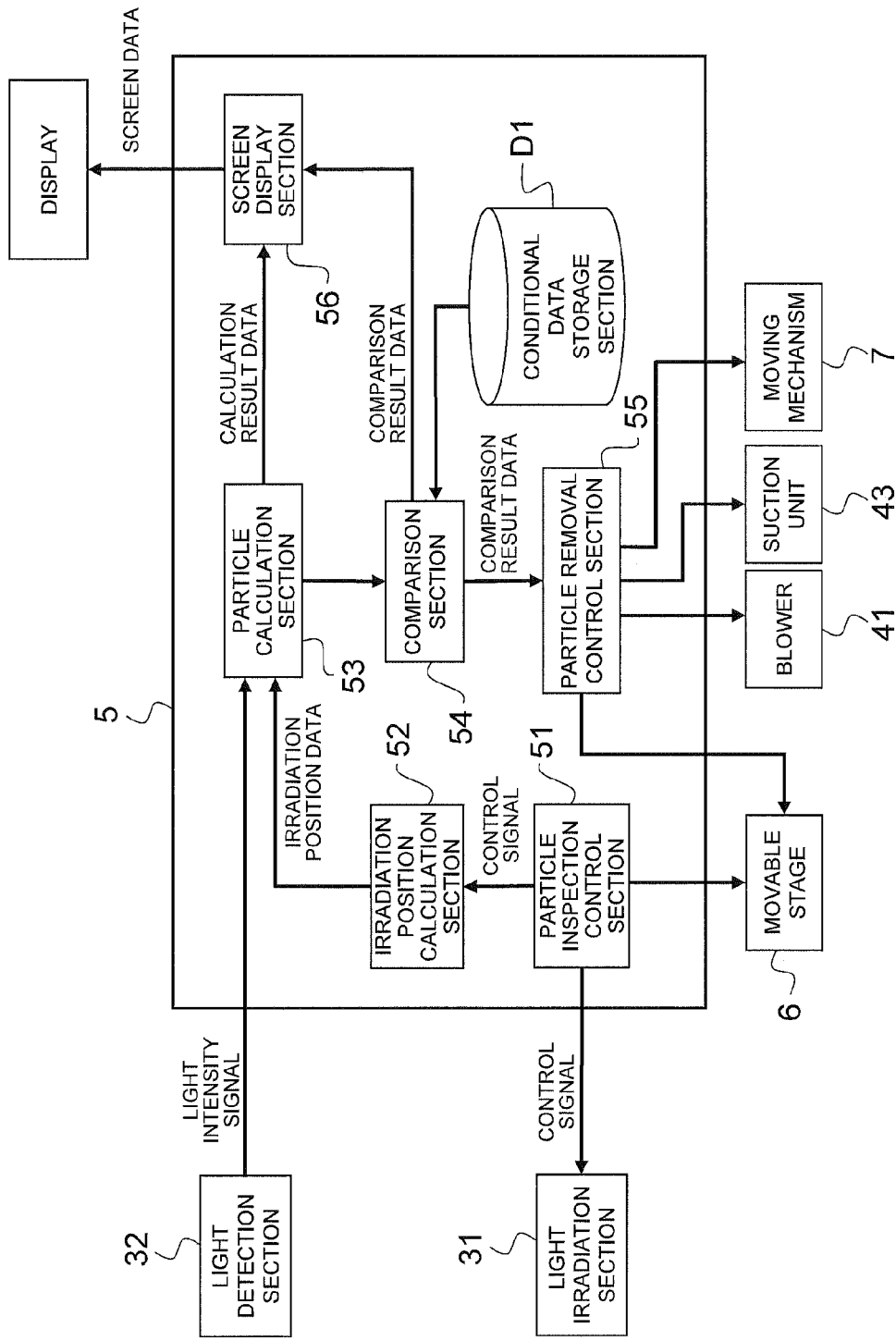
FIG. 4 is a functional configuration diagram of an information processing device according to the embodiment.

The particle removal section 4 removes a particle adhering onto the substrate surface W1 by blowing off gas (such as air, inert gas or gas mixed with liquid drop (mist)) onto the substrate surface W1. As shown in FIG. 3, the particle removal section 4 includes a nozzle 42 in which a blow port for blowing off the air from a blower 41 to outside and an inlet port absorbing the external air by a suction unit 43. The nozzle 42 is connected to the blower 41 and the suction unit 43 by flexible pipes 44, respectively. The blower 41 and the suction unit 43 are provided outside of the mount 2. The nozzle 42 is provided to be movable while being kept opposed to the substrate surface W1 by a moving mechanism 7.

The moving mechanism 7 holds the nozzle 42 so as to strike the gas blown out from the nozzle 42 against the substrate surface W1 perpendicularly and to keep a distance between the blow port of the nozzle 42 and the substrate surface W1 constant according to a type of the substrate W serving as the particle inspection target or a region (set for every circuit pattern). More specifically, the moving mechanism 7 moves the nozzle 42 step by step to a height position corresponding to each of or one of a standard of a size or the like of the substrate W and presence or absence of a pellicle, thereby keeping constant the distance between the blow port of the nozzle 42 and the substrate surface W1. The moving mechanism 7 is specifically configured to include a rail member 71 extending perpendicularly (that is, extending in the Z direction), a fixing member 72 which slidably moves the rail member 71 and to which the nozzle 42 is fixed, and a drive section (not shown) including an actuator such as a stepping motor or a servo motor for moving the fixing member 72 relatively to the rail member 71. The drive section is controlled by the particle removal control section 55 of the information processing device 5 to be described later.

The information processing device 5 controls the movable stage 6 and the light irradiation section 31, receives a light intensity signal from each light detection section 32, and calculates particle information on the substrate surface W1. In addition, the information processing device 5 controls the movable stage 6, the blower 41, and the moving mechanism 7 based on the obtained particle information. As a hardware configuration, the information processing device 5 is a general-purpose or dedicated computer including a CPU, an internal memory, an external memory, an input/output interface, an AD converter and the like. The CPU and peripherals of the CPU operate based on a program stored in a predetermined region of the internal memory or external memory, whereby the information processing device 5 functions as the particle inspection control section 51, an irradiation position calculation section 52, a particle calculation section 53, a conditional data storage section D1, a comparison section 54, the particle removal control section 55, a screen display section 56, and the like.

The particle inspection control section 51 controls the movable stage 6 at constant velocity in the Y direction, and controls a moving angle of the scanning mirror 31b. In addition, the particle inspection control section 51 outputs control signals to the movable stage 6 and the scanning mirror 31b, respectively, and also outputs the control signals to the irradiation position calculation section 52.

The irradiation position calculation section 52 calculates a Y-direction position of the movable stage 6 from the control signals obtained from the particle inspection control section 51, calculates a light irradiation position on the substrate surface W1 from the moving angle of the scanning mirror 31b, and outputs irradiation position data that is data on the light irradiation position to the particle calculation section 53.

The particle calculation position 53 receives the light intensity signal obtained when the inspection light is irradiated and the irradiation position data, and calculates particle information on the substrate surface W1. Examples of the particle information include presence or absence of a particle on the substrate surface W1, a magnitude of the particle, and a position of the particle as well as each of or one of the number of particles on the entire surface W1 and the number of particles in each region, a particle density ((the number of particles)/area (area of each region or unit area)), and (the number of particles)×magnitude/area (area of each region or unit area). The particle calculation section 53 outputs particle information data indicating the particle information as a calculation result to the screen display section 56 and to the comparison section 54.

Figure 5:
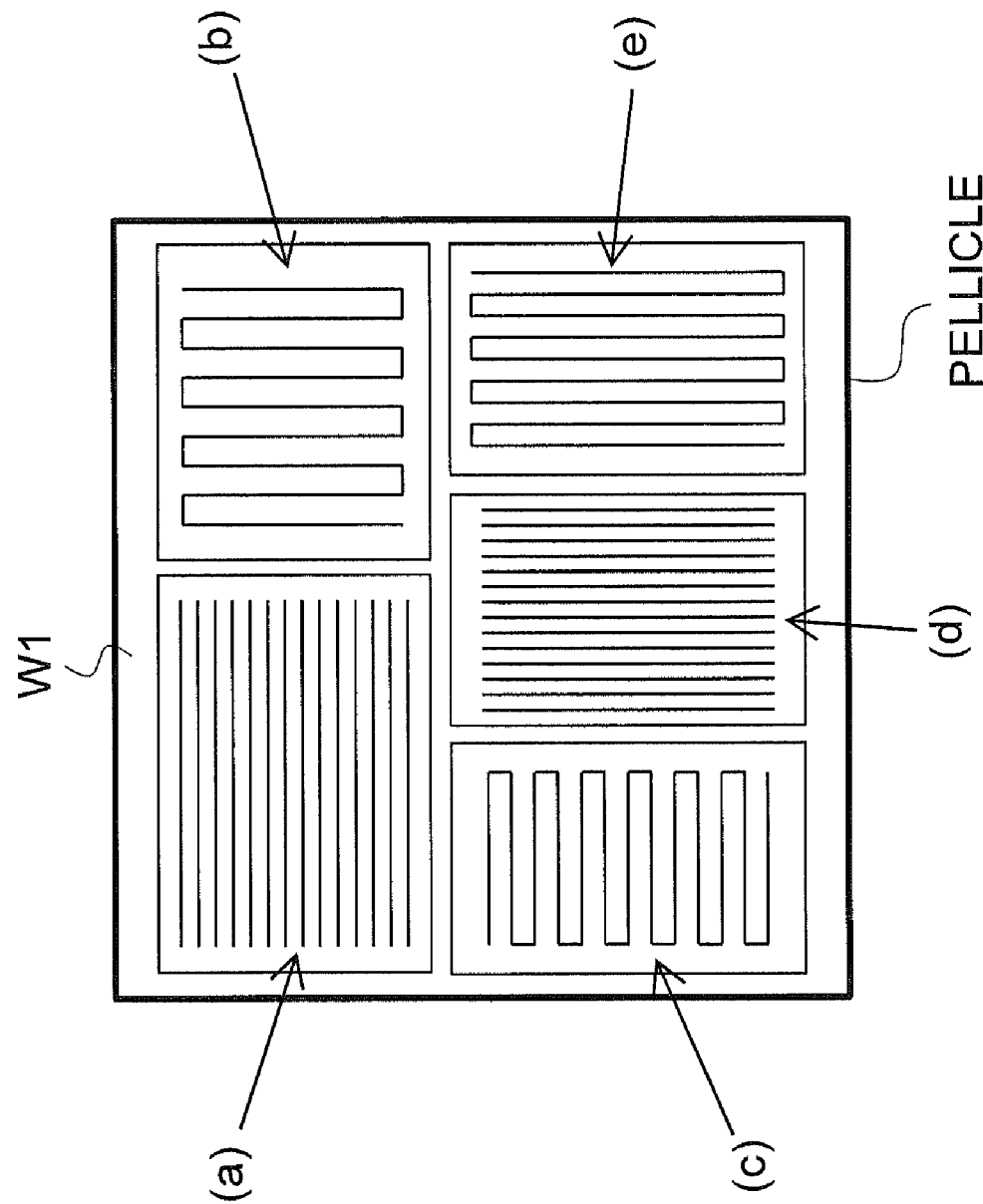
FIG. 5 is a pattern diagram showing various regions of a reticle.

The conditional data storage section D1 stores therein conditional data indicating conditions for particle removal in each region on the substrate surface W1. The conditional data storage section D1 in the present embodiment stores threshold data indicating a threshold for particle removal. As shown in FIG. 5, the threshold for particle removal is set for at least two regions defined according to a circuit pattern or a density (size) of the circuit pattern formed on the reticle. In the present embodiment, the threshold means an allowed magnitude of a particle by which magnitude the particle is allowed to adhere onto the substrate surface W1 in the regions. As the magnitude of the particle, an area, a maximum length or the like of the particle, for example, can be used. For example, in a region of a fine circuit pattern ((a) or (b) in FIG. 5), the allowed magnitude (threshold) of the particle is set small. In a region of a coarse circuit pattern ((b), (c) or (e) in FIG. 5), the magnitude (threshold) of the particle is set large. It is to be noted the particle inspection and removal apparatus 100 can automatically set the regions according to circuit patterns or the like or a user can arbitrarily set the regions. Furthermore, the user can set the regions of the substrate surface W1 and the threshold for every region in advance, and data on the regions and that on the threshold are stored in the conditional data storage section D1.

The comparison section 54 compares the particle information with the threshold for every region. The comparison section 54 receives the particle information data from the particle calculation section 53, acquires the threshold data from the conditional data storage section D1, and compares the magnitude of the particle indicated by the particle information for every region with the threshold set for the region. The comparison section 54 outputs comparison result data indicating a comparison result to the particle removal control section 55. If the screen display section 56 displays the comparison result, the comparison section 54 also outputs the comparison result data to the screen display section 56.

The particle removal control section 55 controls the blower 41, the moving mechanism 7, and the movable stage 6 based on the comparison result received from the comparison section 54. Specifically, if the comparison result indicates that the particle adhering onto a predetermined region exceeds the threshold set for the predetermined region (the magnitude of the particle is larger than the threshold), the particle removal control section 55 controls the movable stage 6 to move the nozzle 42 to the predetermined region so as to remove the particle adhering onto the predetermined region.

Furthermore, the particle removal control section 55 controls the moving mechanism 7 to set the distance between the substrate surface W1 and the blow port of the nozzle 42 to a predetermined distance at which distance the particle removal control section 55 can exhibit a particle removal performance according to the type of the substrate W input in advance. The blower 41 blows off the air onto the predetermined region from the blow port of the nozzle 42, thereby removing the adhering particle. In addition, the suction unit 43 absorbs the particle removed from the blow port of the nozzle 42. At this time, the particle removal control section 55 controls the blower 41 to continuously blow off the air onto the substrate surface W1 while scanning the surface W1 by the nozzle 42. Moreover, the particle removal control section 55 controls the blower 41 and the suction unit 43 to adjust a flow rate of the air blown off from the blow port of the nozzle 42, and to adjust a flow rate of the air absorbed by the inlet port of the nozzle 42. By doing so, it is possible to optimally blow off the air onto various types of substrates W and absorb the particles adhering onto the various types of substrates W.

The screen display section 56 receives the particle information data, that is, calculation result data from the particle calculation section 53 and displays the calculation result on a screen. The screen display section 56 can also receive the comparison result data from the comparison section 54 and display only the particle the magnitude of which exceeds the threshold as a result of the comparison on the screen.

Operation performed by the particle inspection and removal apparatus 100 according to the present embodiment will next be described.

First, the pellicle-added reticle (substrate W) used for exposure is mounted on the movable stage 6 accommodated in the mount 2 of the particle inspection and removal apparatus 100.

Thereafter, the particle inspection control section 51 controls the movable stage 6 and the light irradiation section 31, thereby scanning the inspection light. The particle calculation section 53 calculates the particle information on the substrate surface W1 based on the reflected and scattered light obtained at this time. The comparison section 54 acquires the particle information data obtained by the calculation and the threshold data, and compares the magnitude of the particle included in the particle information with the threshold for every region. The particle removal control section 55 determines whether or not it is necessary to remove the particle for every region.

If the comparison result indicates that the size of the particle is larger than the threshold, the particle removal control section 55 controls the blower 41, the movable stage 6, and the moving mechanism 7 to blow off the air onto a region onto which the particle the magnitude (size) of which exceeds the threshold adheres, thereby removing the particle.

Thereafter, to determine whether or not the particle is surely removed, the particle inspection control section 51 controls the movable stage 6 and the light irradiation section 31, thereby making a particle inspection again.

It is preferable to repeat the above-stated steps a plurality of times so as to improve particle removal reliability. The times of repetition can be set according to the type of the substrate W. At this time, the times of repetition can be set for every type of the substrate W in advance, and repetition data indicating the times of repetition can be stored in the memory so as to be able to make automatic determination and repetition.

The particle inspection and removal steps are preferably executed after end of an exposure step using the pellicle-added reticle (substrate W) and before the substrate W is accommodated in a substrate accommodation case (not shown) accommodating therein the substrate W. While the particle adhering onto the substrate surface W1 is more difficult to remove with passage of time, the particle can be easily removed by removing the particle right after the end of the exposure step.

Advantages of the Embodiment

The particle inspection and removal apparatus 100 according to the present embodiment configured as stated above determines whether to remove a particle for every region of the substrate surface W1 by setting the threshold for each region of the substrate surface W1 and removing the particle only if the magnitude of the particle exceeds the threshold. It is possible to dispense with unnecessary particle removal operation. Therefore, the number of times of cleaning of the substrate W including the particle removal operation can be reduced, working time can be prevented from being prolonged, and running cost can be reduced. In addition, the particle inspection and removal apparatus 100 automatically determines the magnitude of the particle without causing the user to make such a determination. Therefore, it is possible to eliminate determination error of each user. Besides, not the user but the particle inspection and removal apparatus 100 performs the removal operation mechanically. This can lessen burden on the user, reduce risk of damage of the substrate W, and dispense with removal skill.

MODIFICATIONS

The present invention is not limited to the embodiment stated above.

For example, a section including a microscope can be used in place of the light scattering particle information acquisition section as the particle information acquisition section 3 to acquire a surface image.

In the embodiment, the substrate is the pellicle-attached reticle. Alternatively, the particle inspection and removal apparatus can perform particle inspection and removal using, as the substrate, a reticle without a pellicle or a substrate of an arbitrary type such as a semiconductor substrate or a glass substrate.

Moreover, in the embodiment, one information processing device 5 controls the particle information acquisition section 3 and the particle removal section 4. Alternatively, dedicated information processing devices can be provided to correspond to the particle information acquisition section 3 and the particle removal section 4, respectively, and signals can be transmitted or received between the information processing devices.

Further, in the embodiment, the movable stage 6 and the moving mechanism 42 relatively move the particle removal section 4 with respect to the substrate W in the XYZ directions. Alternatively, only the moving mechanism 42 can be used. In this alternative, the moving mechanism 42 includes an X-direction moving mechanism, a Y-direction moving mechanism, and a Z-direction moving mechanism moving the nozzle 42 in the X, Y, and Z directions, respectively. Needless to say, only the movable stage 6 can be used to relatively move the nozzle 42. In this case, it is possible to dispense with the moving mechanism 7 for moving the nozzle 42.

In the embodiment, the threshold is the magnitude of the particle. Alternatively, the number of particles included in each region, a density of particles included in each region or the like can be used as the threshold. In another alternative, a combination of at least two out of the magnitude of the particle, the number of particles included in each region, and the density of particles can be used as the threshold.

In the embodiment, the threshold is set as conditions for particle removal and the particle is removed if the magnitude of the particle is larger than the threshold. Alternatively, a shape of the particle, a range of the magnitude of the particle or the like can be used as the conditions. If the shape of the particle is used as the conditions, then a predetermined value of, for example, an aspect ratio (major side/minor side) of the particle is set as the threshold, and it suffices to remove a particle having an aspect ratio higher than the threshold. In this way, by setting the threshold for the aspect ratio, it is possible to focus on removing particles, such as threads, easy to remove.

Moreover, in the embodiment, the particle information acquisition section 3 and the particle removal section 4 are provided only on one surface (an upper surface) of the substrate W and only the one surface (upper surface) of the substrate W is subjected to particle inspection and particle removal. Alternatively, the particle information acquisition section 3 and the particle removal section 4 can be provided on each of both surfaces of the substrate W so that one surface (the upper surface) and the other surface (a lower surface) of the substrate W can be subjected to particle inspection and particle removal.

Furthermore, the particle information acquisition section 3 can further include an acquisition region setting section that sets a region on which the particle information acquisition section 3 acquires the particle information, the particle information acquisition section 3 can acquire particle information only on the region set by the acquisition region setting section, and the comparison section 54 makes a comparison for the set region. In another alternative, the comparison section 54 can further include a comparison region setting section that sets a region for which the comparison section 54 makes a comparison, and the comparison section 54 can make a comparison only for the region set by the comparison region set by the comparison region setting section. The region set by the acquisition region setting section or the comparison region setting section is, for example, a region to which a particle tends to adhere or a region where a circuit pattern is fine. To make setting, the particle inspection and removal apparatus 1 can automatically make settings or the user can arbitrarily make settings. Even if the particle inspection is intended to a part of the substrate W, the particle removal ranges over the entire substrate surface W1. By doing so, it is possible to reduce particle inspection time.

In the embodiment, the particle removal section 4 removes the particle by blowing off the gas onto the substrate surface W1. Alternatively, a particle adhering onto the substrate surface W1 can be removed using a needle having a sharpened needle point.

In the embodiment, the particle removal control section 55 keeps constant the distance between the substrate surface W1 and the blow port of the nozzle 42 irrespectively of the type of the substrate W. Alternatively, the distance between the substrate surface W1 and the blow port of the nozzle 42 can be changed according to the type of the substrate W.

Moreover, in the embodiment, the particle inspection and removal apparatus 100 is configured to integrally provide the particle information acquisition section 3 and the particle removal section 4. Alternatively, the particle inspection and removal apparatus 100 can be configured to provide the particle information acquisition section 3 and the particle removal section 4, to combine the particle information acquisition section 3 and the particle removal section 4 by, for example, transporting the substrate W between the particle information acquisition section 3 and the particle removal section 4 using a transport mechanism so as to perform particle inspection and particle removal.

In the embodiment, the particle information acquisition section 3 inspects the particle again so as to determine whether or not the particle is surely removed. Alternatively, the particle information acquisition section 3 does not necessarily inspect the particle again.

Needless to say, a part of or all of the embodiment and the modifications can be appropriately combined, and the present invention is not limited to the embodiment and the modifications and can be variously changed or modified without departure from the scope of the concept of the present invention.

What is claimed is:

1. A particle inspection and removal apparatus comprising:
   a particle information acquisition section acquiring particle information on a particle adhering onto a substrate surface;
   a particle removal section removing the particle adhering onto the substrate surface;
   a comparison section comparing a condition for particle removal set for each of a plurality of regions on the substrate surface with the particle information on each of the regions obtained by the particle information acquisition section; and
   a particle removal control section controlling the particle removal section to remove the particle on the substrate surface if a comparison result of the comparison section indicates that the particle information satisfies the condition,
   wherein the substrate is a reticle for transferring a circuit pattern onto a semiconductor wafer or a reticle with a pellicle, and the regions are set for different circuit patterns formed on the reticle.

2. A particle inspection and removal program for inspecting and removing a particle adhering onto a substrate surface using a particle information acquisition section acquiring particle information on a particle adhering onto a substrate surface and a particle removal section removing the particle adhering onto the substrate surface, the particle inspection and removal program causing a computer to function as:
   a comparison section comparing a condition for particle removal set for each of a plurality of regions on the substrate surface with the particle information on each of the regions obtained by the particle information acquisition section; and
   a particle removal control section controlling the particle removal section to remove the particle on the substrate surface if a comparison result of the comparison section indicates that the particle information satisfies the condition,
   wherein the substrate is a reticle for transferring a circuit pattern onto a semiconductor wafer or a reticle with a pellicle, and the regions are set for different circuit patterns formed on the reticle.

* * * * *